(12) United States Patent
Taylor

(10) Patent No.: US 9,707,009 B2
(45) Date of Patent: *Jul. 18, 2017

(54) DELIVERY CAP FOR IMPLANTATION OF A PENILE PROSTHETIC INTO A PENIS

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/245,219

(22) Filed: Aug. 24, 2016

(65) Prior Publication Data

US 2016/0361090 A1    Dec. 15, 2016

Related U.S. Application Data

(63) Continuation of application No. 14/732,678, filed on Jun. 6, 2015, now Pat. No. 9,451,982.

(51) Int. Cl.
| | |
|---|---|
| *A61F 5/00* | (2006.01) |
| *A61B 17/34* | (2006.01) |
| *A61F 2/26* | (2006.01) |
| *A61B 17/06* | (2006.01) |
| *A61B 19/00* | (2006.01) |
| *A61B 17/02* | (2006.01) |
| *A61B 17/00* | (2006.01) |
| *A61B 90/00* | (2016.01) |

(52) U.S. Cl.
CPC .... *A61B 17/3468* (2013.01); *A61B 17/06109* (2013.01); *A61B 17/06166* (2013.01); *A61F 2/26* (2013.01); *A61B 17/0293* (2013.01); *A61B 2017/00473* (2013.01); *A61B 2017/0287* (2013.01); *A61B 2017/06042* (2013.01); *A61B 2017/06085* (2013.01); *A61B 2017/3409* (2013.01); *A61B 2017/3456* (2013.01); *A61B 2019/461* (2013.01); *A61B 2090/062* (2016.02)

(58) Field of Classification Search
CPC   A61F 5/41; A61F 2005/411; A61F 2005/415; A61F 2/26; A61B 17/3468
USPC ..................................................... 600/38–40
See application file for complete search history.

(56) References Cited

U.S. PATENT DOCUMENTS

| | | | |
|---|---|---|---|
| 7,985,176 B1 * | 7/2011 | Morningstar | A61F 2/26 600/40 |
| 9,451,982 B1 * | 9/2016 | Taylor | A61B 17/3468 |
| 2003/0065337 A1 | 4/2003 | Topper et al. | |

(Continued)

FOREIGN PATENT DOCUMENTS

DE    2946833 A1    5/1980

*Primary Examiner* — John Lacyk
(74) *Attorney, Agent, or Firm* — Coloplast Corp., Coloplast A/S; Nick Baumann

(57) ABSTRACT

A system for implanting a penile prosthetic into a penis with an insertion tool includes a penile implant, a tow suture, and a delivery cap. The implant has a proximal end insertable into a crus penis and a distal end insertable into a glans penis. The tow suture is coupled to the distal end of the penile implant. The delivery cap is coupled to the tow suture and a portion of the delivery cap is shaped as a hemispherical dome. The delivery cap has an aperture that is formed in the hemispherical dome, with the aperture sized to allow the needle of the insertion tool to pass through the aperture.

15 Claims, 14 Drawing Sheets

(56) References Cited

U.S. PATENT DOCUMENTS

2004/0167574 A1* 8/2004 Kuyava ............... A61B 17/04
    606/224
2005/0075534 A1* 4/2005 Kuyava ................ A61F 2/26
    600/38

* cited by examiner

US 9,707,009 B2

DELIVERY CAP FOR IMPLANTATION OF A PENILE PROSTHETIC INTO A PENIS

SUMMARY

Penile implants have proven useful in treating erectile dysfunction in men. The surgical placement of the implant in the penis can be accomplished through the use of a tow suture. A tool pushes a Keith-style needle to deliver the tow suture through the forward glans penis and the surgeon pulls on the tow suture to draw the penile implant fully within a dilated cavity formed in the penis. Surgeons have expressed that threading the tow suture through the eye of the Keith needle can be difficult, and sometimes the tow suture will slide out of the eye of the Keith needle or out of the tool during the implantation procedure. Surgeons would welcome improvements to the placement of implants within the penis.

The delivery cap described below operates to allow a needle associated with an insertion tool to automatically capture a tow suture secured to a penile implant.

One aspect provides a system for implanting a penile prosthetic into a penis, the system comprising: a penile implant having a proximal end insertable into a crus penis and a distal end insertable into a glans penis; a tow suture removably secured to the distal end of the penile implant; a delivery cap coupled to the tow suture; and an insertion tool having a distal tool end insertable into a corpora cavernosum of the penis and including a needle configured for delivery through the glans penis; wherein the delivery cap has an aperture, with a portion of the tow suture located in the aperture.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
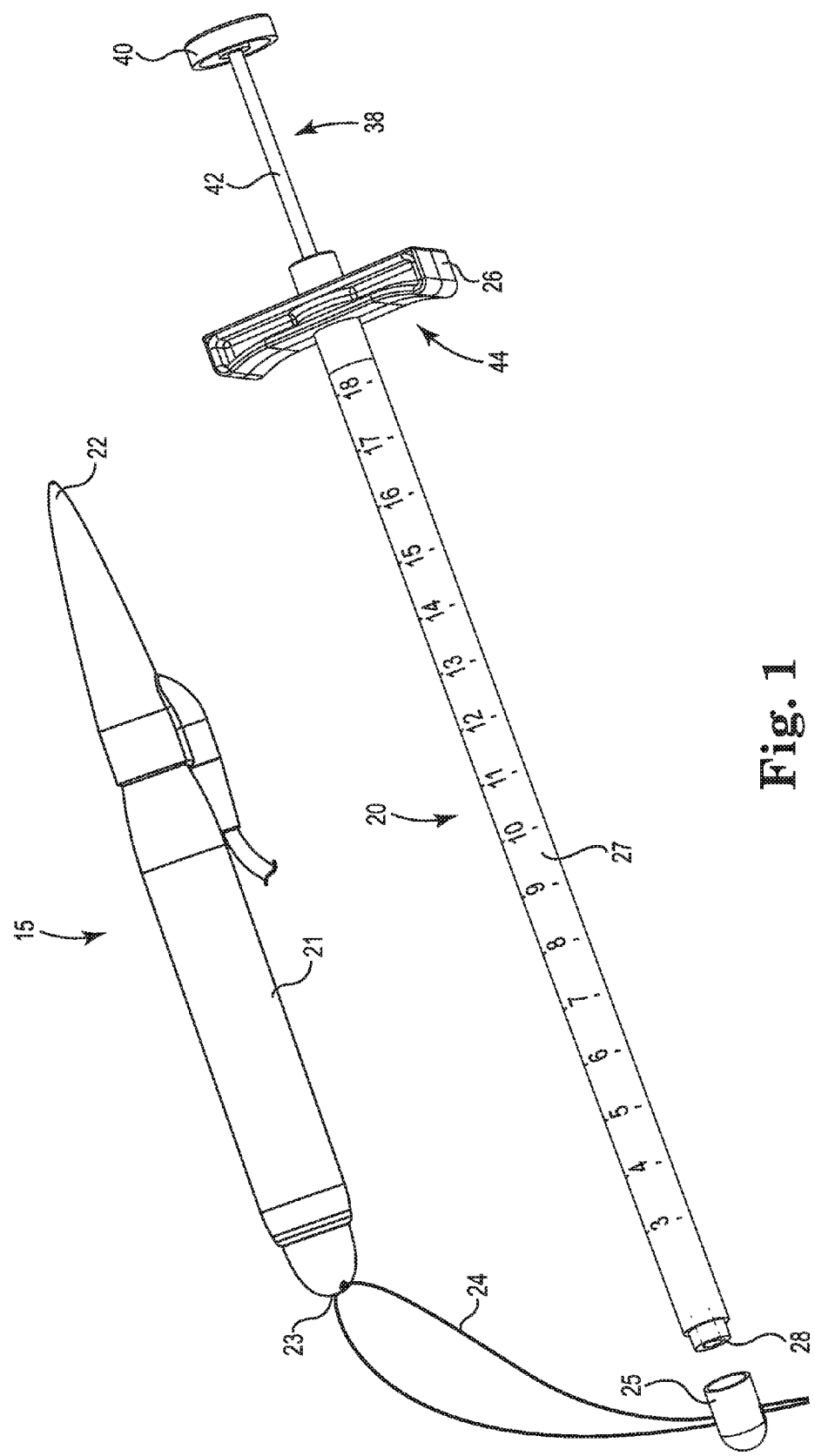
FIG. 1 is a perspective view of one embodiment of a system for implanting a penile prosthetic into a penis including an insertion tool attachable to a delivery cap, with the delivery cap secured to a tow suture coupled to a penile implant.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments disclosed in this application, may be combined with each other ("mixed and matched"), unless specifically noted otherwise.

End means endmost. Relative to an observer, for example a surgeon, a distal end is the furthest endmost location of a distal portion of a thing being described, and a proximal end is the nearest endmost location of a proximal portion of the thing being described. The portion next to or adjacent to an end is an end portion.

A surgically implanted penile prosthetic has proven useful in treating erectile dysfunction in men. One acceptable implantable penile prosthetic includes two inflatable cylinders implanted in the penis, a pump implanted in the scrotum or other internal space of the body, and a liquid holding reservoir implanted in the abdomen or other internal space of the body.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is inserted into a bore of the Furlow introducer. The Keith needle could possibly fall out of the bore of the Furlow introducer, so the surgical staff handles the tool with care. The surgeon steadies the Furlow introducer with one hand and pushes a plunger (or obturator) of the Furlow introducer with the other hand to push the needle out of the bore. Pushing the plunger pushes the needle distally from of the introducer, through tissue of the penis, and out the glans penis. The exposed portion of the needle is handled by the surgeon. The needle is advanced out of the glans penis, the suture is removed from the needle, and the needle is discarded. The remaining suture is subsequently employed to tow the cylinder from the incision into the glans penis within the dilated corpora cavernosum.

The above-described procedure has proven effective when implanting penile prostheses. However, surgeons would appreciate having fewer parts to handle during the procedure and would welcome a tool that reduces or eliminates exposure to the sharp end of the Keith needle.

Embodiments provide a tool for measuring a length of the penis distally (forward toward the glans) and proximally (rearward toward the crus) to determine a suitable length for the implantable prosthetics.

Embodiments provide a tool with additional functionality over a Furlow introducer. Specifically, the tool is capable of both ejecting the needle forward through tissue and retrieving the needle backward into a bore of the tool. Retraction of the needle into the bore of the tool could potentially reduce exposure of the staff to the sharp end of the Keith needle.

Embodiments provide a needle that is secured to the tool and biased to move into and out of the bore of the tool to reduce the possibility of the needle undesirably falling away from the tool. Needles that fall out of the tool can become non-sterile if the needle leaves the sterile field and can possibly lead to an undesirable increased risk of needle sticks.

Embodiments provide a delivery cap that is connected at the time of manufacture to a tow suture, where the tow suture is connected to a penile implant. The delivery cap operates to allow a needle associated with an insertion tool to automatically capture the tow suture during implantation of the penile implant, which relieves the surgeon or the surgical staff from threading the suture through the needle.

FIG. 1 is a perspective view of one embodiment of a system 15 suitable for implanting a penile prosthetic into a penis with an insertion tool 20. The system 15 includes a penile implant 21 having a proximal end 22 insertable into a crus penis and a distal end 23 insertable into a glans penis, a tow suture 24 coupled to the distal 23 end of the penile implant 21, and a delivery cap 25 coupled to a tow suture 24. The delivery cap 25 is "pre-loaded" onto the tow suture 24 that has been inserted through the implant 21. The delivery cap 25 is attachable to the insertion tool 20 as the surgeon prepares to place the implant into the penis. The insertion tool 20 has a needle that extends from the tool 20 to push the tow suture 24 through the glans penis. The delivery cap 25 is configured to position the tow suture 24 so that the needle will engage with the tow suture 24 as the needle exits the insertion tool 20. In this way, the delivery cap 25 automatically engages the tow suture 24 with the needle as the system 15 is used, which is convenient for the surgical staff.

The delivery cap 25 is secured to the tow suture 24 at the time of manufacture and the cap 25 is configured to mate with the insertion tool 20 after the system 15 is removed from its packaging. The cap 25, after it is attached to the tool 20, ensures that the preloaded needle 30 inside of the tool 20 will engage with the tow suture 24 to automatically deploy the tow suture 24 as the needle 30 is pushed out of the tool 20. The system 15 obviates the process of the surgeon attaching the tow suture to the needle, which saves time in surgery. The system 15 complements the TITAN® Penile Implant available from Coloplast Corp., Minneapolis, Minn.

Figure 2:
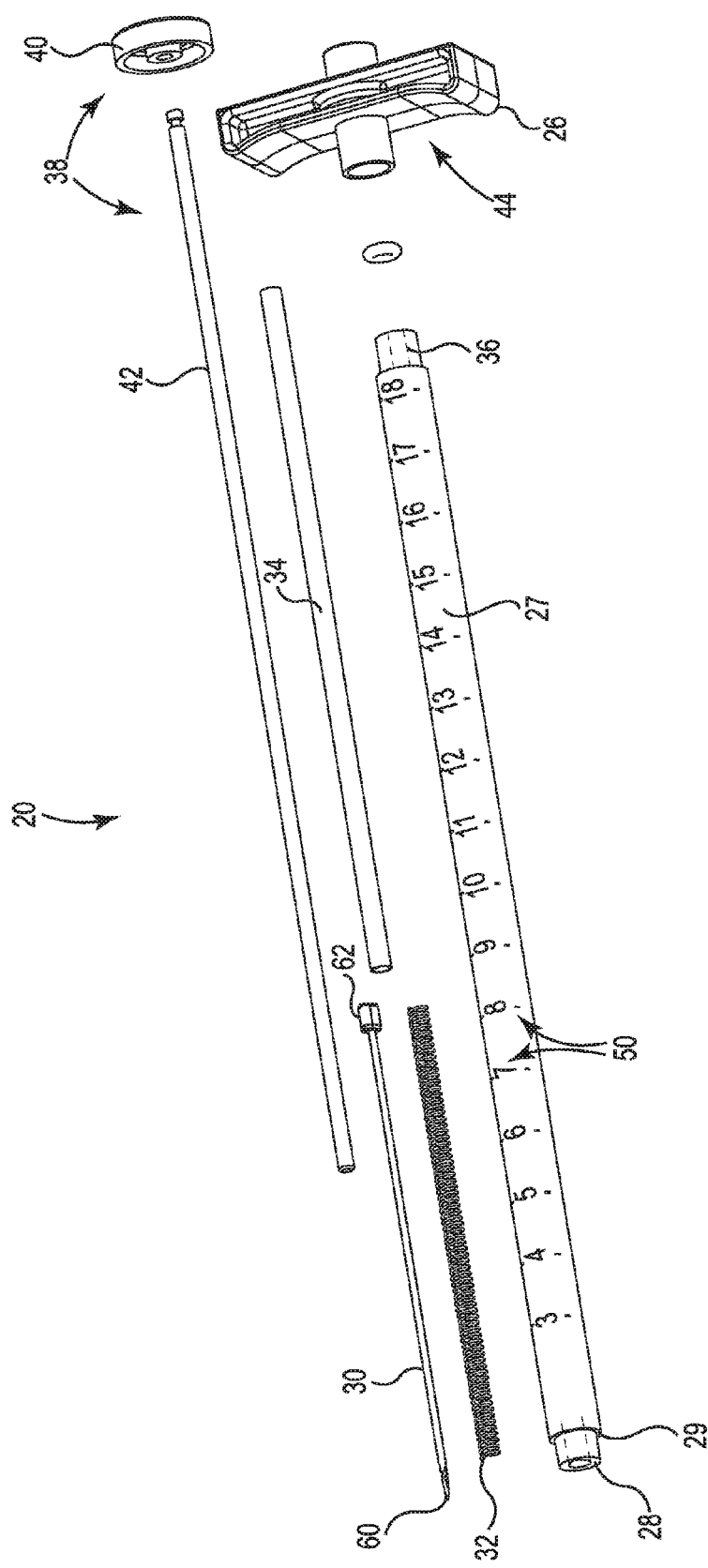
FIG. 2 is a perspective exploded view of the insertion tool illustrated in FIG. 1.

FIG. 2 is a perspective exploded view of the insertion tool 20. The tool 20 includes an o-ring that is located between a handle 26 and a shaft 27, a distal tool end 28 located at a distal end of the shaft 27, a needle 30, a spring 32, a needle stopper 34 that is retained in a bore 36 of the shaft 27, and a plunger assembly 38 including a button 40 attached to a rod 42. The rod 42 is insertable through the handle 26 and into the bore 36 of the shaft 27 and is operable to move a sharp point of the needle 30 outward from and back into the distal tool end 28 of the tool 20.

The o-ring is suitably fabricated from an elastomeric material and is located between the handle 26 and the shaft 27 to seal and provide a guide for the rod 42.

The handle 26 includes a curvature 44 that accommodates the fingers when the tool 20 is held in a hand. The button 40 is sized to receive the thumb when the fingers cradle the curvature 44 of the handle 26.

The shaft 27 is provided with indicia 50 printed or etched or marked on at least one side surface of the shaft 27 to indicate a length extending away from the distal tool end 28. In one embodiment, the indicia 50 are marked on multiple side surfaces of the shaft 27 for convenient viewing at any angle. The tool 20 is preferably disposable, so one suitable material for the shaft 27 includes a polymer such as an extruded polycarbonate or polypropylene or other high performance, low cost plastic material. In one embodiment, the indicia 50 measure centimeters a distance away from the distal tool end 28, which allows the surgeon to measure the length of the corpora cavernosum and select an appropriately sized penile prosthetic. The distal tool end 28 is provided with a stepped shoulder 29 that is sized to receive and capture the delivery cap 25 (FIG. 1). The bore 36 of the shaft 27 exits at an opening formed in the distal tool end 28 to allow the needle 30 to exit the shaft 27 when the plunger assembly 38 is moved in a distal direction.

The needle 30 includes a pointed distal end 60 opposite from a head 62. The spring 32 is sized to be positioned coaxial on the needle 30 between the pointed distal end 60 and the head 62. The spring 32 provides a biasing force to retract the needle 30 back into the shaft 27 of the tool 20. The rod 42 moves through the needle stopper 34 to push against the head 62 to move the needle in a distal direction. One suitable rod 42 is a stainless steel rod, although a polymer rod having a suitable column strength is also acceptable. When the pushing force is removed from the plunger assembly 38, the spring 32 biases the head 62 of the needle 30 in a proximal direction until the head 62 runs up against (abuts) the needle stopper 34. The length of the needle stopper 34 is sized to ensure that the pointed distal end 60 of the needle 30 is retained in an unexposed position within the shaft 27 of the tool 20 until the plunger assembly 38 is activated. The spring 32 allows the surgeon to selectively move the needle 30 out of the shaft 27 by pushing on the button 40. Releasing the button 40 causes the spring 32 to bias the needle 30 back into the shaft 27.

In one embodiment, the spring 32 is optional and is not included, and instead the needle 30 is integrated as one piece with the rod 42. The monolithic needle 30/rod 42 forms a plunger that is operated manually by the surgeon, where forward movement of the integrated needle 30/rod 42 delivers the suture through the glans penis and rearward retraction of the integrated needle 30/rod 42 retrieves the needle 30 back into the shaft 27.

Figure 3:
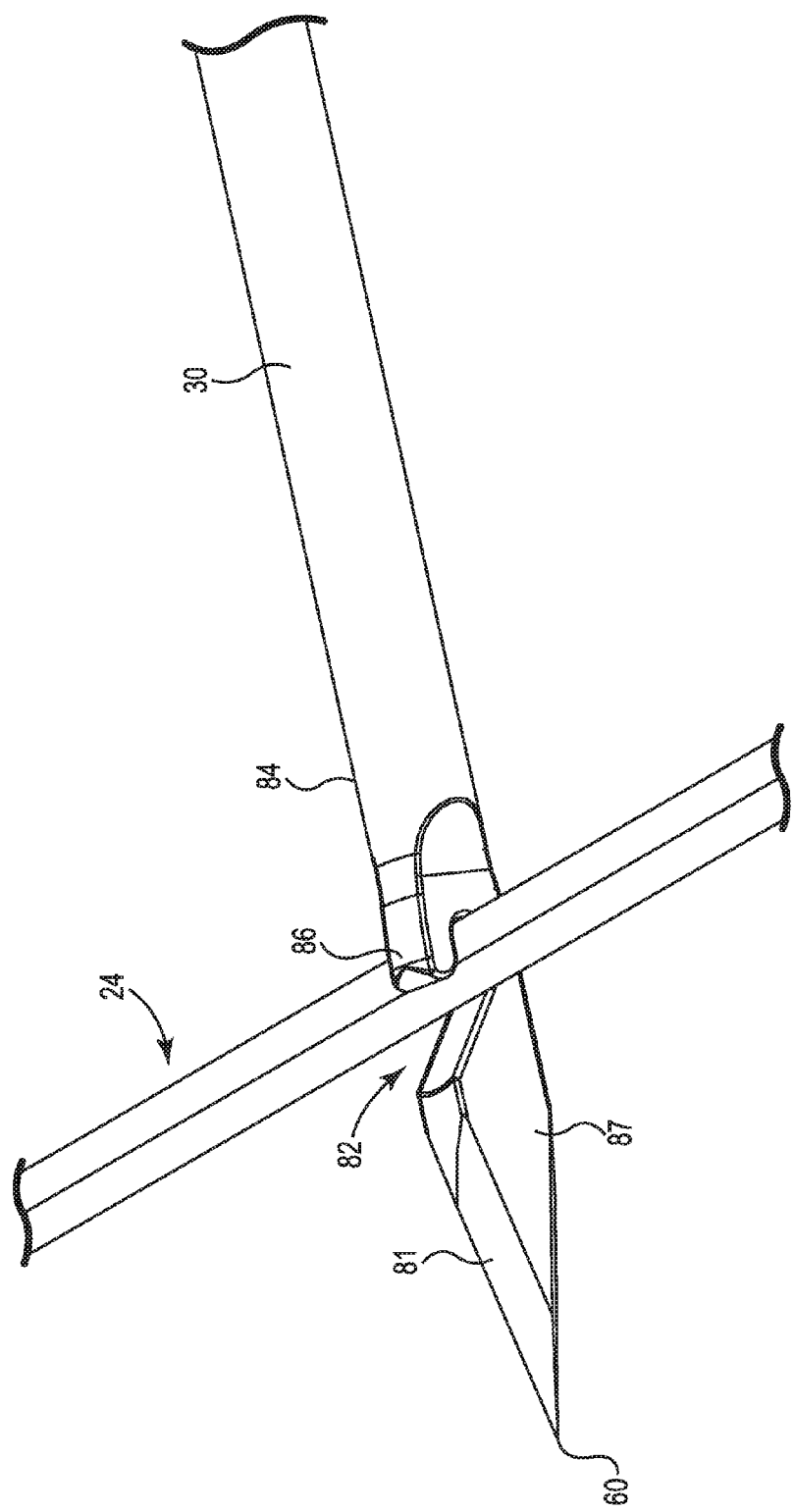
FIG. 3 is a perspective view of one embodiment of a needle of the insertion tool illustrated in FIG. 2.

FIG. 3 is a perspective view of the needle 30 as it would appear when engaged with the suture 24. Pushing on the plunger assembly 38 (FIG. 2) pushes the pointed distal end 60 of the needle 30 through the delivery cap 25 that is secured to the distal tool end 28 of the tool 20, and this movement engages the needle 30 with the suture 24 that is staged in a capture position within the delivery cap 25.

In one embodiment, the needle 30 includes multiple cutting surfaces including an inclined cutting surface 81 extending in a proximal direction away from the pointed distal end 60, an opposing declined cutting surface opposite of the inclined surface 81, and opposed cutting faces. An open slot 82 is formed in an exterior surface 84 of the needle 30. The open slot 82 provides an opening to receive the suture 24 after the pointed end 60 and the cutting surface 81 pass though the delivery cap 25. The open slot 82 is distinguished from an eye of a needle in that a needle eye is a closed geometric opening. Dexterity and excellent vision is called upon to thread a small diameter suture through a small eye of a needle. In contrast, the open slot 82 allows the suture 24 to automatically drop into the open slot 82 as the needle passes through the delivery cap 25, which provides for immediate and positive engagement between the needle 30 and the suture 24. This approach reduces the amount of handling that is done with the needle 30 and is more convenient and easier than threading a suture strand into an eyelet of a Keith needle.

In one embodiment, the needle 30 includes a projection 86 that projects over a portion of the open slot 82. The projection 86 operates to capture and retain the two thread portions of the suture 24 when the needle 30 is pushed in a distal direction through the delivery cap 25. The projection 86 operates to subsequently allow the suture 24 to exit the open slot 82 when the needle is retracted in a proximal direction back into the shaft 27 of the tool 20.

In one embodiment, side portions 87 of the needle 30 are flattened to provide a relief space relative to the shaft 27 of the tool 20, which allows the suture 24 to have a lower profile when lying against the needle 30.

The penile implant 21 and the delivery cap 25 are both engaged with the tow suture 24 when manufactured. One suitable penile implant 21 includes the TITAN® Penile Implant available from Coloplast Corp., Minneapolis, Minn. In one embodiment, the suture 24 is provided as a single strand that is inserted through an eyelet or hole of the penile implant 21, where the single strand of the suture 24 is doubled to provide a tow suture having two portions with increased tensile strength compared to the single strand. In a later step of the implantation procedure, the two thread portions operate as a tow rope to pull the penile implant 21 into a dilated corpora cavernosum, as described below.

Figure 4:
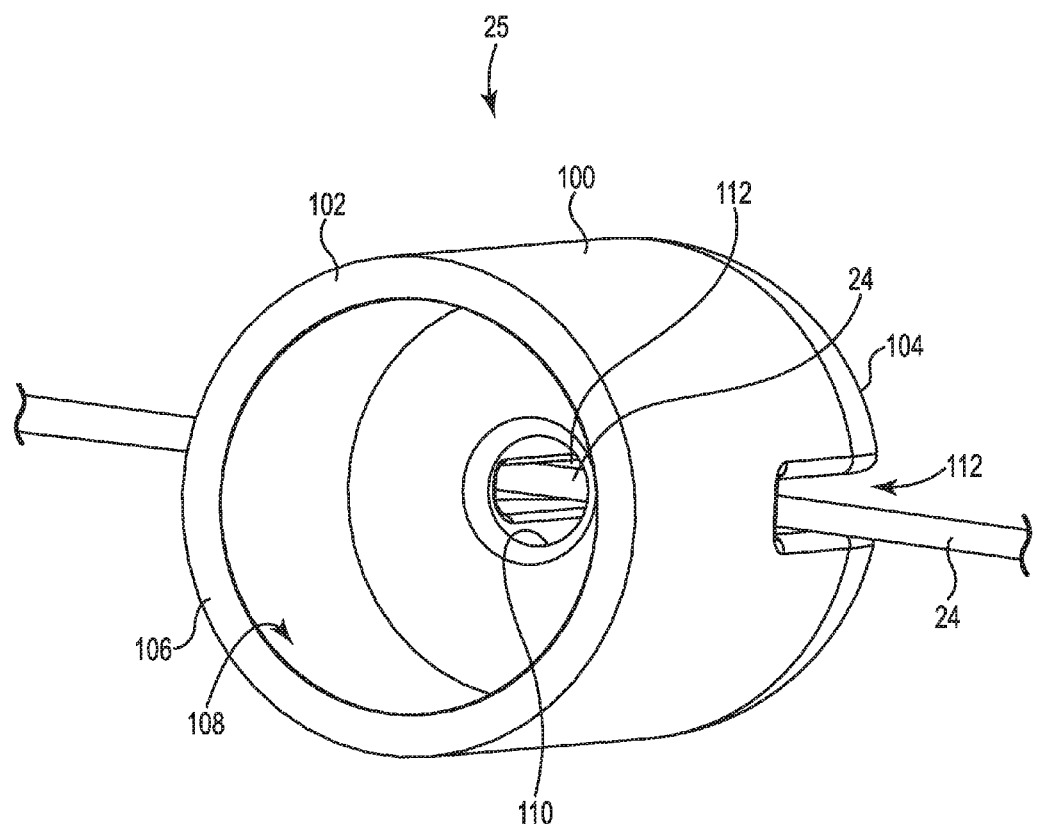
FIG. 4 is a perspective view of one embodiment of a proximal end of the delivery cap illustrated in FIG. 1.

FIG. 4 is a perspective view of a proximal end of the delivery cap 25. The delivery cap 25 has an exterior side surface 100 extending between a proximal end 102 and a distal end 104. The proximal end 102 defines a proximal base 106 that is formed to include a recess 108 that is sized to fit over the distal tool end 28 (FIG. 1) of the insertion tool 20. An aperture 110 extends longitudinally through the delivery cap 25. The aperture 110 is configured to present a portion of the tow suture 24 within the aperture 110 in a manner that ensures engagement between the tow suture 24 and the needle 30 (FIG. 2). In one embodiment, a slotted opening 112 is formed through the distal end 104 of the delivery cap 25. The slotted opening 112 is sized to receive and position the tow suture 24 within the aperture 110.

In one embodiment, the aperture 110 extends longitudinally through the delivery cap 25, and the slotted opening 112 extends laterally from one end of the exterior side surface 100 to the opposing end of the exterior side surface 100, such that the slotted opening 112 intersects with and is perpendicular to the aperture 110.

Figure 5:
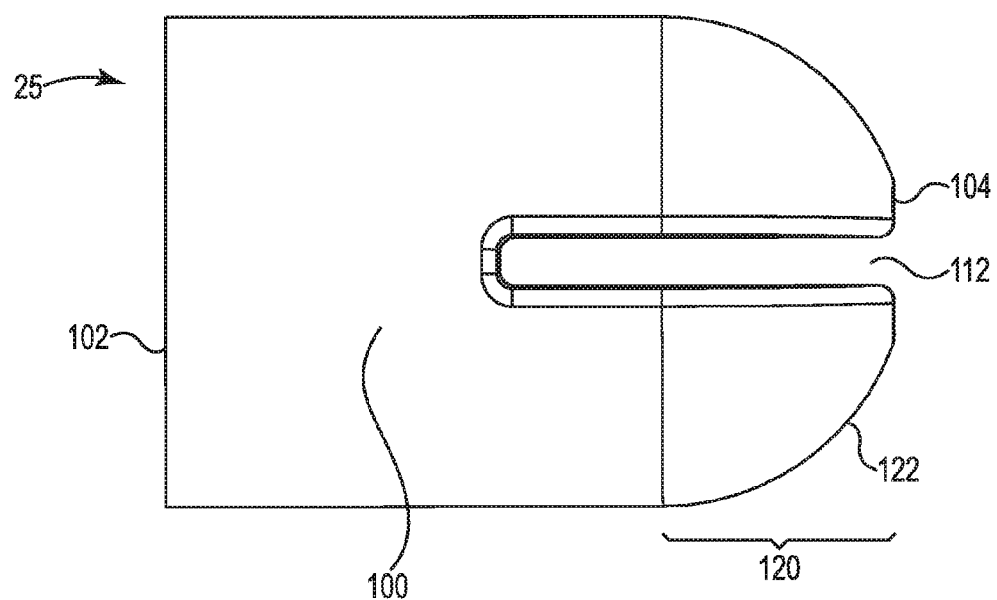
FIG. 5 is a side view of the delivery cap.
Figure 6:
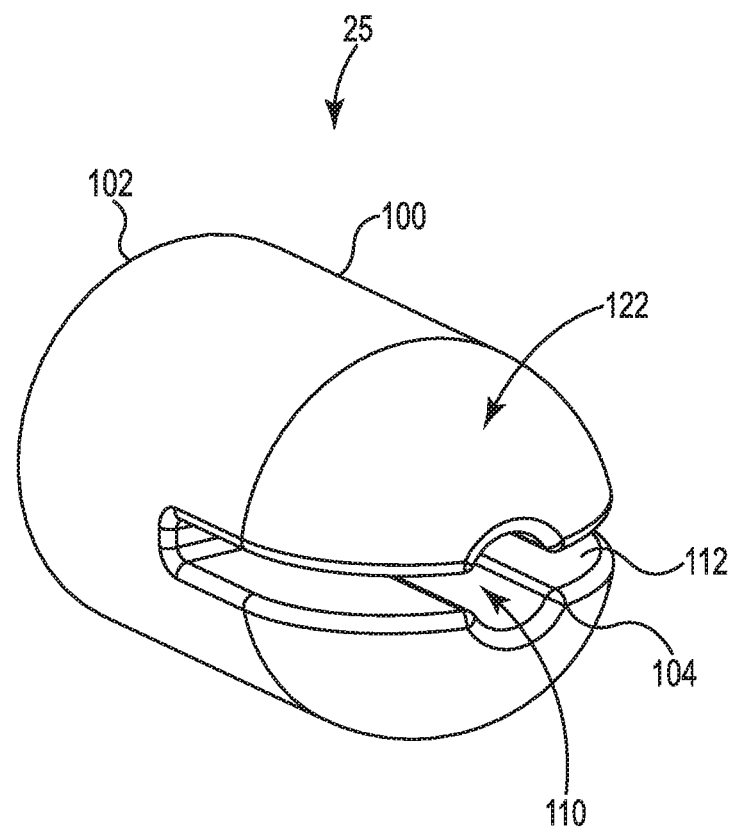
FIG. 6 is a perspective view of a distal end of the delivery cap.

FIG. 5 is a side view and FIG. 6 is a perspective view of the delivery cap 25. In one embodiment, a distal end portion 120 of the delivery cap 25 is shaped as a hemispherical dome 122. The hemispherical dome 122 is smoothly curved in three dimensions to fit in a comfortable and appropriate manner within the dilated corpora cavernosum of the penis. The slotted opening 112 is formed in the distal end 104 of the delivery cap 25. The slotted opening 112 is provided to secure and position the tow suture 24 across the aperture 110 (FIG. 4). For this reason, it is desirable that a depth of the slotted opening 112 is at least two times the diameter of a strand of the tow suture 24. Suitable depths of the slotted opening 112 are in a range from 0.1 to 0.75 inches.

In one embodiment, the exterior side surface 110 of the delivery cap 25 is circular and has an outside diameter that is equal to an outside diameter of the shaft 27 of the insertion tool 20 (FIG. 2).

Figure 7:
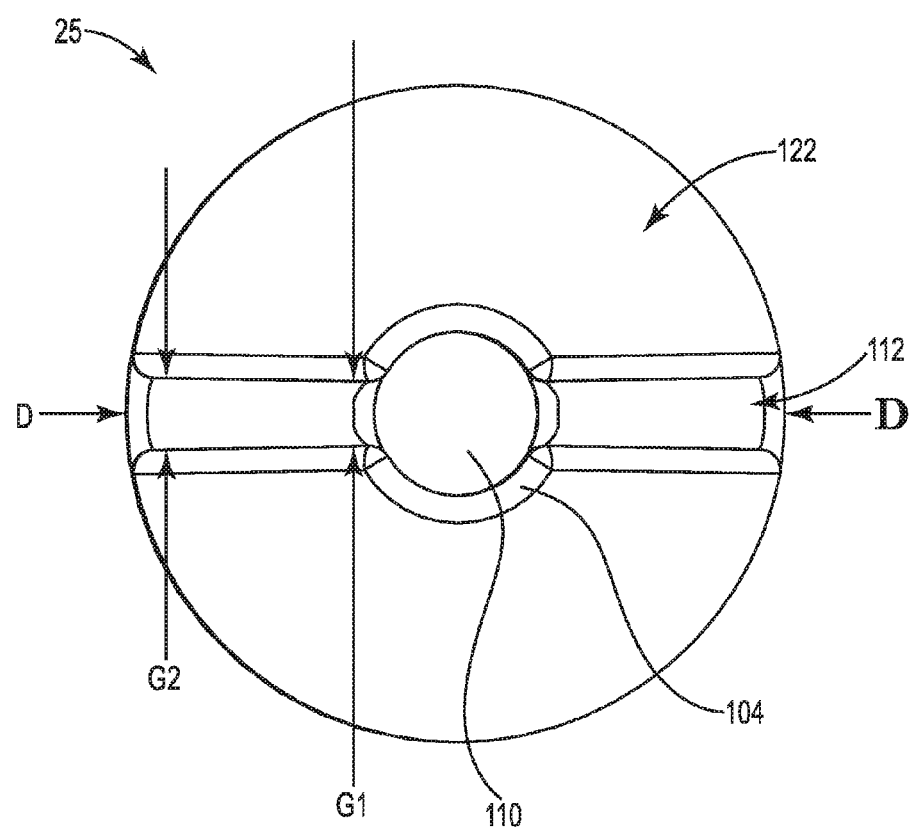
FIG. 7 is a distal end view of the delivery cap.

FIG. 7 is an end view of the distal end 104 of the delivery cap 25. The slotted opening 112 extends laterally across a diameter D of the delivery cap 25. The aperture 110 extends longitudinally through a length of the delivery cap 25. The slotted opening 112 is positioned to secure the tow suture 24 within the aperture 110. In one embodiment, the slotted opening 112 is tapered to converge from the outside diameter D down to the aperture 110 to ensure that the slotted opening 112 pinches against the tow suture 24. In one embodiment, the slotted opening 112 is tapered to have a gap G1 measured where the slotted opening 112 meets with the aperture 110 that is smaller than a gap G2 measured at the outside diameter D of the delivery cap 25. It is acceptable to provide the slotted opening with a gap having a uniform gap distance, particularly if the uniform gap distance is sized to retain the inserted tow suture 24.

Figure 8:
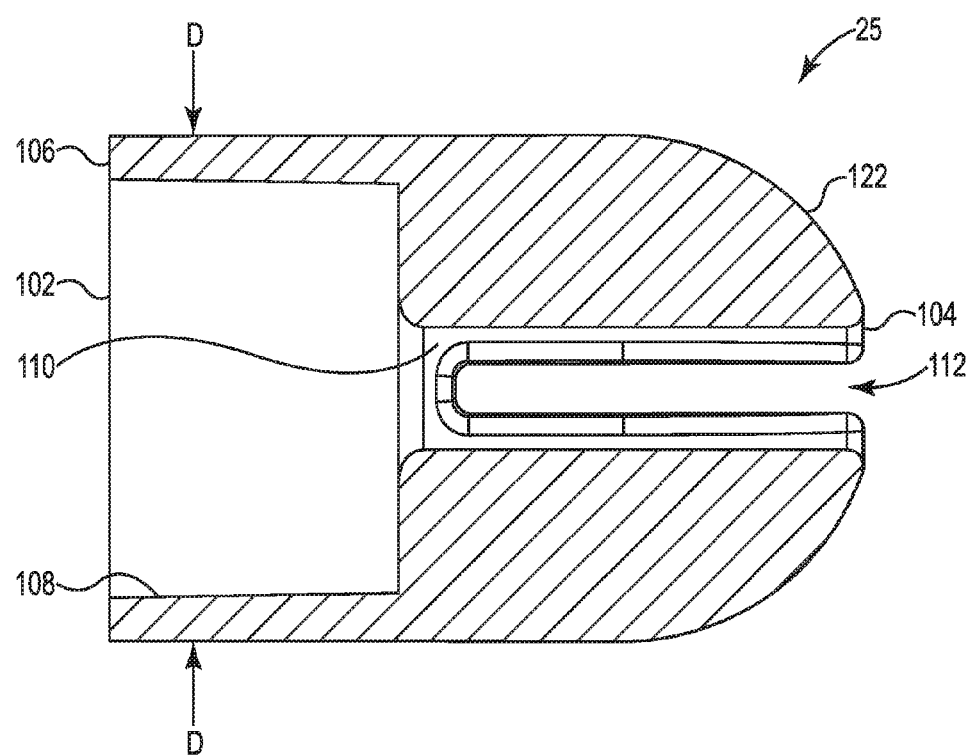
FIG. 8 is a cross-sectional view of the delivery cap.
Figure 9:
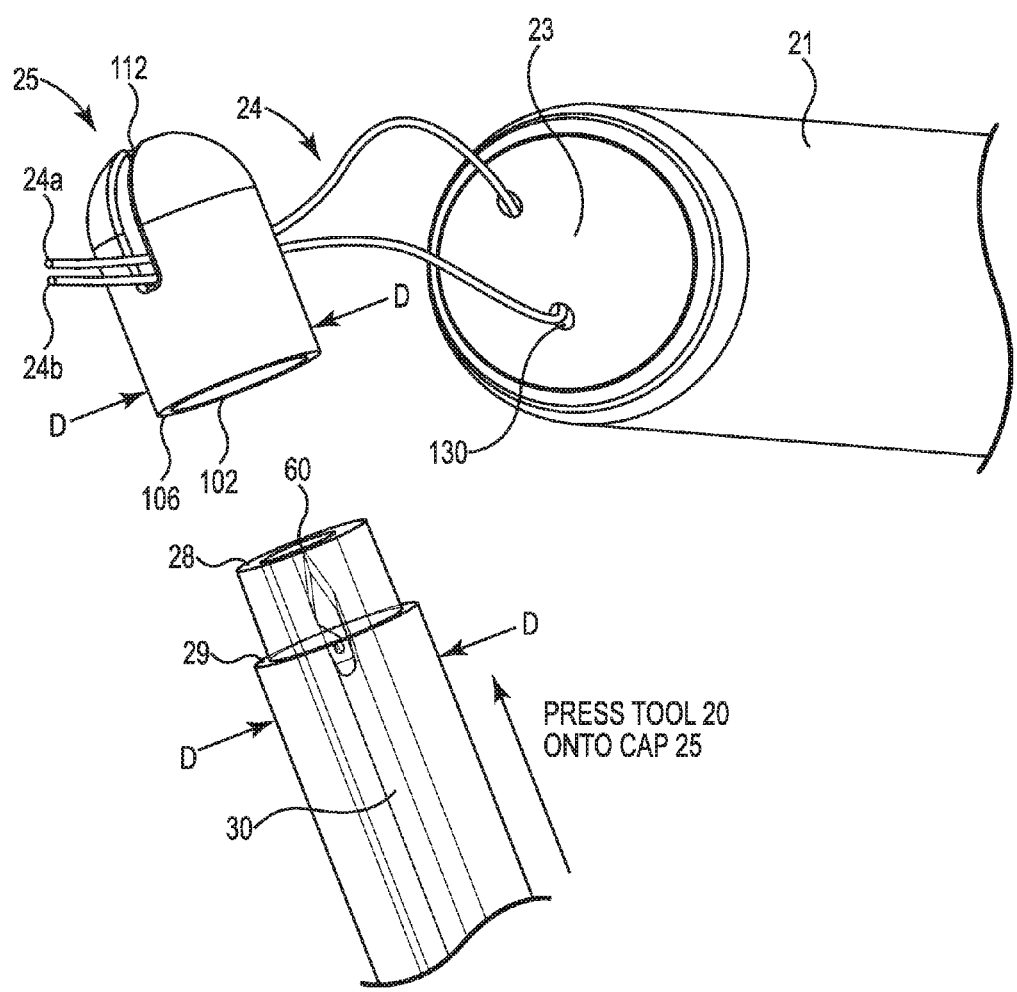
FIG. 9 is a perspective view of the delivery cap aligned for attachment with the insertion tool.

FIG. 8 is a cross-sectional view of the delivery cap 25, and FIG. 9 is a perspective view of attachment of the delivery cap 25 to the insertion tool 20. The delivery cap 25 is sized to have an outside diameter D that mates to the outside diameter D of the shaft 27 of the insertion tool 20. The proximal base 106 and the recess 108 are sized to fit over the distal tool end 28 and against the stepped shoulder 29 of the insertion tool 20. In one embodiment, the entrance to the aperture 110 that is formed in the recess 108 is smoothly curved, as is the entrance to the slotted opening 112.

The proximal end 102 of the delivery cap 25 is attachable to the distal tool end 28 of the insertion tool 20 and the slotted opening 112 is formed in the distal end 104 of the delivery cap. The aperture 110 is a located at a center of the delivery cap 25 and communicates from the proximal end 102 to the distal end 104 of the delivery cap.

The delivery cap 25 is sized to be snapped in place on the distal tool end 28 of the insertion tool 20. In one embodiment, the delivery cap 25 is sized to resist removal or detachment from the insertion tool 20, particularly as the insertion tool 20 and the delivery cap 25 (when attached) are removed from the corpora cavernosum of the penis. It is desirable that the delivery cap 25 is sized to fit on only those style of tools 20 that have been manufactured to be compatible with the cap 25 to reduce the possibility of employing the cap 25 with non-standard or non-Coloplast tools.

In one embodiment, the aperture 110 is a central aperture located on a centreline of the delivery cap 25, and a portion of the tow suture 24 is retained in the central aperture to ensure that the needle 30 will engage with the tow suture 24 during needle deployment.

In one embodiment, the tow suture 24 is a single strand of suture that is inserted through a hole 130 formed in the distal end 23 of the penile implant 21 to provide two free ends 24a, 24b of the single strand of suture 24. The delivery cap 25 is coupled to the tow suture 24 between the distal end 23 of the penile implant 21 and the two free ends 24a, 24b of the single strand of suture 24. After placement of the penile implant 21 in the penis, either one of the two free ends 24a, 24b may be pulled and removed out of the hole 130 to separate the suture 24 from the penile implant 21.

Figure 10:
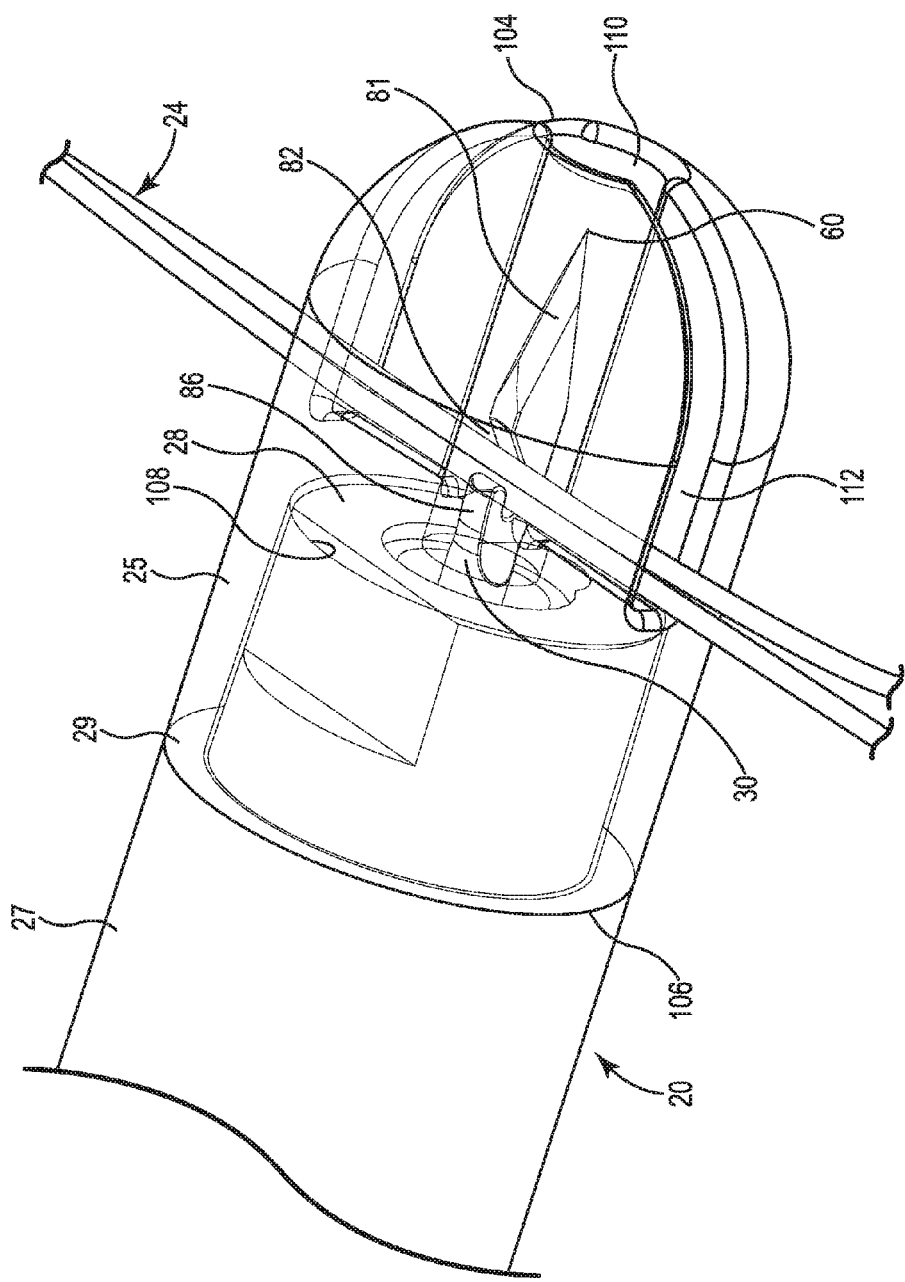
FIG. 10 is a perspective view of the delivery cap attached to the insertion tool with a needle of the tool advanced into engagement with the tow suture.

FIG. 10 is a perspective view of the delivery cap 25 attached to the insertion tool 20. The proximal base 106 of the delivery cap 25 has been pushed over the distal tool end 28 and into engagement with the stepped shoulder 29. The recess 108 formed in the delivery cap 25 fits over the distal tool end 28 of the insertion tool 20. The slotted opening 112 holds the suture 24 within the aperture 110 to ensure that the needle 30 will engage with the tow suture 24 when the needle 30 moves through the delivery cap 25.

The assembled insertion tool 20 and the delivery cap 25 are inserted into the dilated corpora cavernosum of the penis of a patient who has been prepared to receive the penile implant 21. As the needle 30 exits the distal tool end 28, the tow suture 24 will fall into and engage with the open slot 82 in the needle 30. The projection 86 of the needle 30 extends over a portion of the open slot 82 to ensure that the tow suture 24 remains engaged within the open slot 82. The needle 30 is now engaged with the tow suture 24. Additional movement of the needle 30 out of the delivery cap 25 will move the tow suture 24 out of the slotted opening 112 to allow the needle 30 to push the tow suture 24 through the glans penis. The pointed distal end 60 of the needle 30 pierces the glans penis and arrives at a location where the surgeon may grasp the tow suture 24. Retraction of the needle 30 back into the insertion tool 20 allows the tow suture 24 to disengage from the open slot 82. The portion of the tow suture remains projecting out of the glans penis as the insertion tool 20 is removed from the penis.

FIG. 11-FIG. 14 are schematic views of a procedure for implanting the penile implant 21 into a penis P.

The penis P is reclined against the torso. The groin area of the patient is shaved, cleaned and suitably prepped with a surgical solution prior to draping with a sterile drape in accordance with the healthcare provider's procedures. A retraction device, such as those available from Lone Star Medical Products of Stafford, Tex., is placed around the penis P if so desired by the surgeon to establish the surgical field. A catheter 150 is inserted into the urethra U from the distal end (or glans) 152 of the penis P. Thereafter, the surgeon forms an incision to access the corpora cavernosa C1 and C2 of the penis.

Suitable examples of incisions for accessing the corpora cavernosa C1 and C2 include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, the surgeon forms a 2-3 cm transverse incision through the subcutaneous tissue of the median raphe of the upper scrotum Sc and dissects down through the Darto's fascia and Buck's fascia to expose the tunicae albuginea of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The surgeon typically will insert a blunt-ended scissors or other elongated tool to separate a portion of the spongiosum material to open a pathway for dilation and measurement of the corpora cavernosa C1, C2. After suitable dilation, the surgeon measures the length of the corpora cavernosa to determine the suitable size for the penile implant 21. In one approach, the surgeon ensures that the appropriately sized penile implant 21 has been selected by inserting the tool 20 into the corpora cavernosum C1 or C2 and using the indicia 50 to measure the proximal and distal length of each corpora cavernosum C1 and C2. For example, the tool 20 is inserted into one of the corpora cavernosum C1 or C2 forward in the distal penis toward the glans penis and the distal measurement is recorded by reading one of the marks 50. The tool 20 is then inserted into the same corpora cavernosa C1 or C2 rearward in the proximal penis toward the crus of the penis to record the proximal length of the corpora by reading one of the marks 50. The distal and proximal measurements would typically be made in reference to a "stay stitch" temporarily placed in the incision. The sum of the distal and the proximal measurements represent the length of that corpora cavernosum, and this information is used to select the size of the penile implant 21. This procedure is repeated for the other of the corpora cavernosa C1 or C2 to ensure the appropriately sized penile implant 21 has been selected for the companion corpora.

Figure 11:
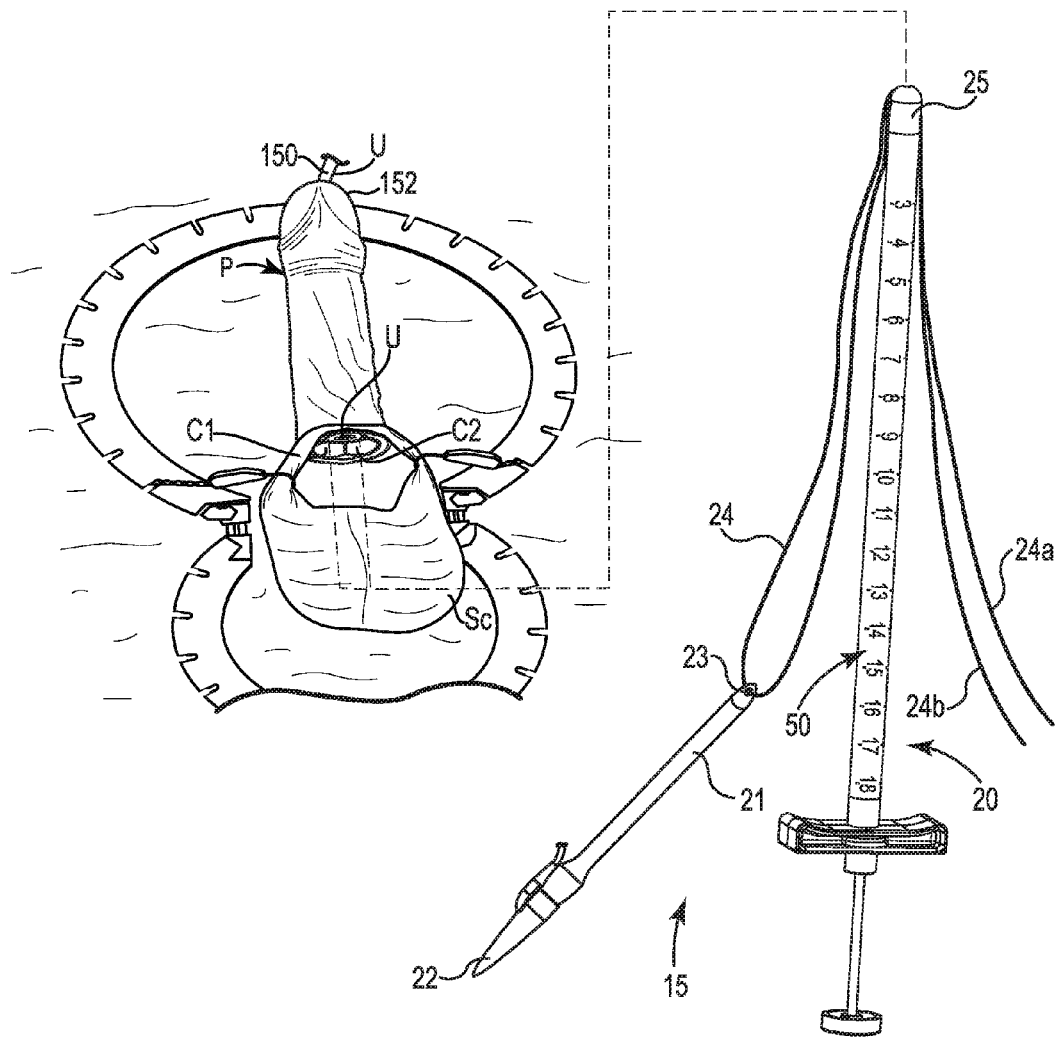
FIG. 11 is a schematic view of the system illustrated in FIG. 1 prepared for implantation of the penile implant.

FIG. 11 illustrates the penis P prepped for surgery and the system 15 prepared for implantation of the penile implant 21 into the corpora cavernosum C2. The suture 24 is attached to the implant 21 and is secured to the delivery cap 25, and the delivery cap 25 is attached to the distal end of the tool 20. The pointed end 60 of the needle 30 is maintained in an unexposed position within the distal tool end 28 of the tool 20 and further isolated by the presence of the delivery cap 25. A portion of the suture 24 is engaged with the slotted opening 112 of the delivery cap 25 with the free ends 24a, 24b of the suture 24 trailing alongside the implant 21.

Figure 12:
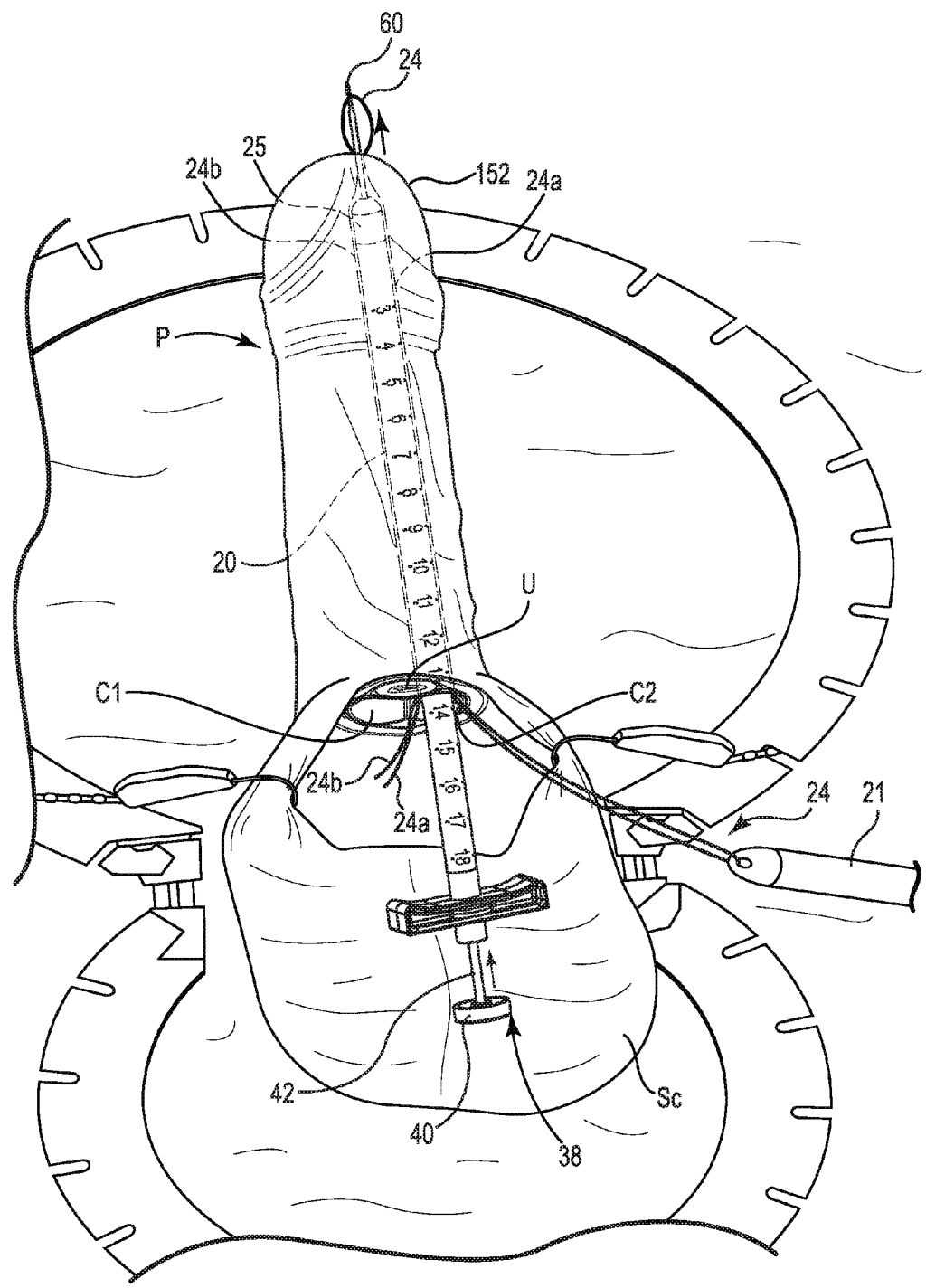
FIG. 12 is a schematic view of the system illustrated in FIG. 11 with the needle of the insertion tool delivering a portion of the suture through a glans of the penis.

FIG. 12 is a schematic view of the tool 20 inserted into the corpora cavernosum C2. The penile implant 21 is outside of the penis P and is attached to the suture 24. The opposite free ends 24a, 24b of the suture 24 extend out of the corpora cavernosum C2 and are available for access by the surgeon. The button 40 of the plunger assembly 38 is moved in a distal direction to advance the pointed end 60 of the needle 30 through the delivery cap 25, where the needle 30 engages with the portion of the suture 24 that is positioned within the aperture 110 (See FIG. 4). The portion of the suture 24 within the aperture 110 is pushed through the glans penis by the needle 30. The button 40 is released and the pointed end 60 of the needle 30 is biased back into the shaft 27 of the tool 20. Upon retraction of the pointed end 60 of the needle 30 into the tool 20, the suture 24 is ejected out of the open slot 82 formed through the exterior surface of the needle 30. The suture 24 will escape from the open slot 82 when the needle 30 is moved in the proximal direction, particularly as the suture 24 meets resistance from the glans penis 104. The surgeon employs a forceps or other tool to grasp the portion of the suture 24 that is exposed exterior to the penis P.

Figure 13:
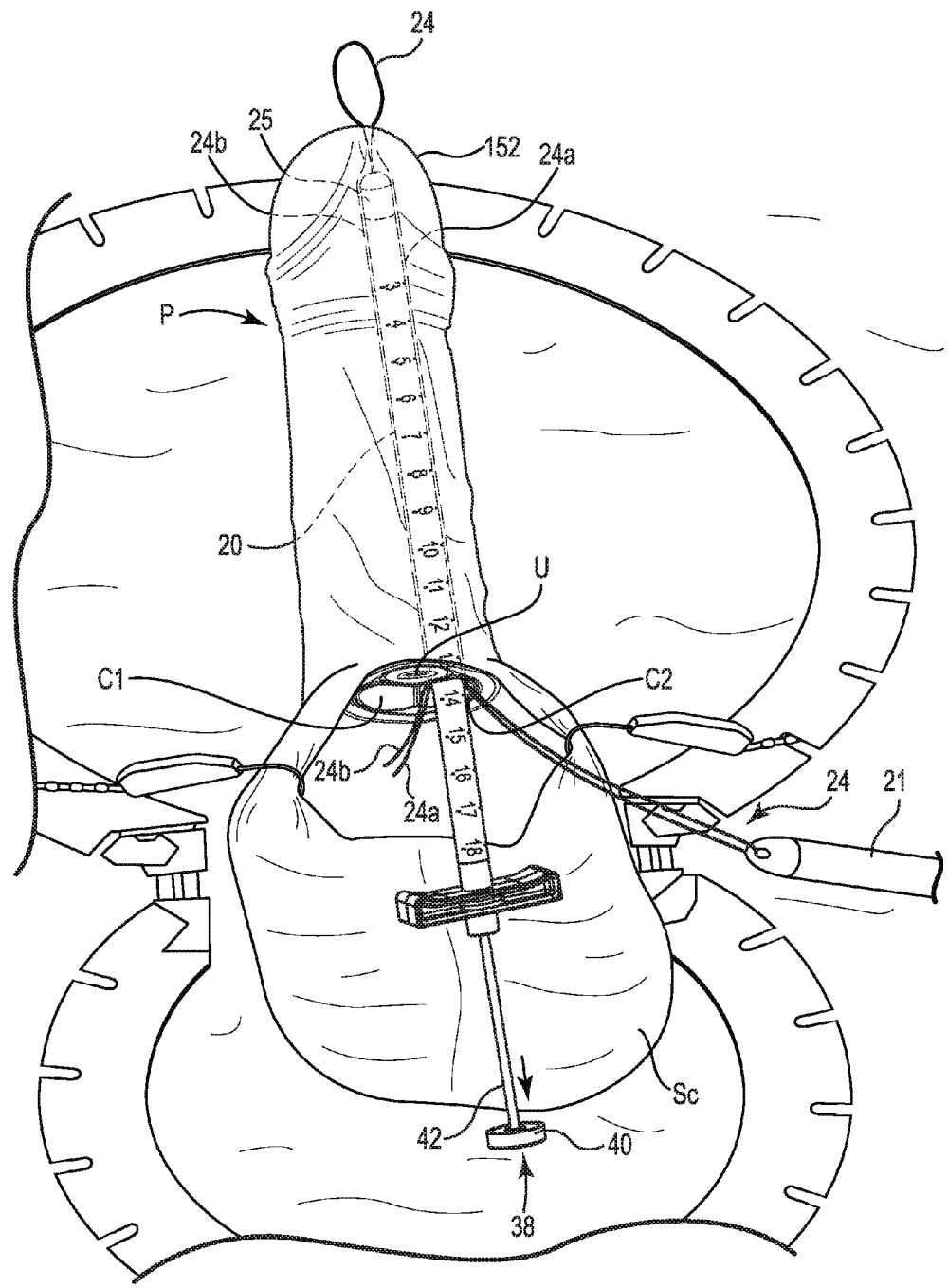
FIG. 13 is a schematic view of the system illustrated in FIG. 12 with the suture delivered exterior to the penis and the needle retracted into the insertion tool.

FIG. 13 illustrates that the force applied to the plunger assembly 38 has been relaxed. The plunger assembly 38 has moved in a proximal direction, and the spring 32 has biased the pointed end 60 of the needle 30 into the unexposed position within the distal tool end 28. The exposed part of the suture 24 has been pushed from the open slot 82 of the needle 30 and remains outside the glans penis 104. The needle 30 has been retracted into the distal tool end 28 of the tool 20. The tool 20 may now be removed from the corpora cavernosum C2.

Figure 14:
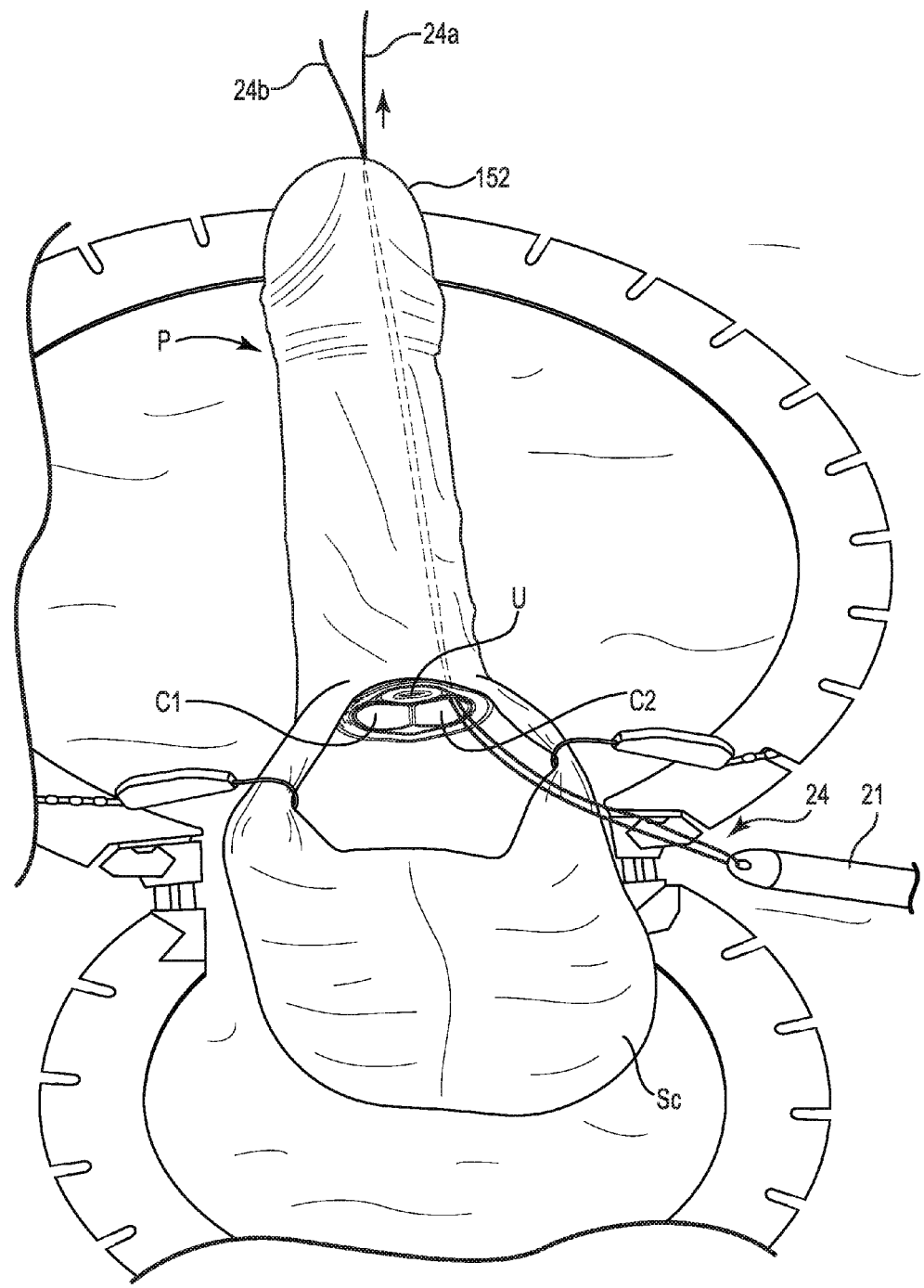
FIG. 14 is a schematic view of the penile implant being towed by the tow suture to a location within a dilated corpora cavernosum of the penis.

FIG. 14 illustrates that the suture 24 is employed to tow the penile implant 21 distally into the corpora cavernosum C2 up to the glans penis. The implant 21 is placed in the corpora cavernosum and the suture 24 is removed from the hole 130 or the eyelet 130 of the implant 21.

The proximal end of the penile implant 21 is suitably implanted proximately into the crus penis.

A second penile prosthetic is implanted in the corpora cavernosum C1 following the steps described above for implantation of the penile implant 21 the corpora cavernosum C2.

One acceptable method of implanting a penile prosthetic using the system 15 includes:

Manufacture components including a tow suture attached to an implant and a delivery cap attached to the tow suture;

Provide an insertion tool having a distal end sized to engage with the delivery cap;

Connect the delivery cap to the insertion tool;

Insert the tool and the delivery cap into a dilated corpora;

Press the plunger and push the needle through the delivery cap and through the glans penis, where the needle engages with a portion of the tow suture captured in the delivery cap;

Allow the needle to retract in a proximal direction and then grasp tow suture as it disengages from the needle;

Allow the needle to fully retract, remove the tool from the corpora, and maintain the tow sutures exterior to the glans penis;

Pull on the tow sutures to bring the implant fully into the corpus, then pull the suture out of the implant and out of the corpus;

Repeat for the second implant in the second corpus.

When the delivery cap is attached to the distal tool end, the portion of the tow suture located in the aperture is aligned with the needle with the advantage of ensuring the needle will (or must or cannot avoid) engagement with the tow suture.

A slotted opening is formed in a distal end of the delivery cap to advantageously couple and secure the tow suture.

A slotted opening is formed in a distal end of the delivery cap and the aperture communicates with the slotted opening with the advantage of ensuring the needle will engage with the tow suture.

A slotted opening is formed in a distal end of the delivery cap with the slotted opening extending laterally across an entire diameter of the delivery cap with the advantage of ensuring the needle will engage with the tow suture as the needle traverses the delivery cap.

A slotted opening is formed in a distal end of the delivery cap with the slotted opening extending laterally across an entire outside diameter of the delivery cap, with a first gap formed in the slotted opening that is measured where the slotted opening intersects with the aperture crafted to be smaller than a second gap formed in the slotted opening that is measured where the slotted opening intersects with the outside diameter of the delivery cap. The narrower first gap advantageously ensures that the slotted opening will capture/secure and prevent the tow suture from slipping out of the slotted opening.

The delivery cap includes a proximal base having a recess that is sized to fit over the distal tool end of the insertion tool to provide the advantage that the delivery cap is custom fitted to this style of tool, thus preventing the use of unauthorized or non-functional tools.

A distal end portion of the delivery cap is shaped as a hemispherical dome to advantageously fit within the dilated corpora cavernosum.

The delivery cap includes a distal hemispherical dome opposite from a proximal base that is attachable to the distal tool end, and the aperture extends longitudinally through the delivery cap between the proximal base and the distal hemispherical dome to ensure that the needle is directed along a path that will unavoidably result in the needle engaging and coupling with the tow suture as the needle traverses the delivery cap.

The delivery cap includes a distal hemispherical dome opposite from a proximal base that is attachable to the distal tool end, and a slotted opening is formed in the distal hemispherical dome, with the slotted opening coupled with the tow suture to ensure that the needle will engage with the tow suture as the needle traverses the delivery cap.

A slotted opening is formed laterally across an entire diameter of the delivery cap and the aperture is formed longitudinally through the delivery cap with the aperture intersecting the slotted opening to ensure that the needle will engage with the tow suture as the needle traverses the delivery cap.

The delivery cap has an outside diameter that is equal to an outside diameter of the insertion tool to provide the advantage that the delivery cap is custom fitted to this style of tool, to provide comfort to the patient, and to ensure that other non-authorized tools are not employed with the delivery cap.

The tow suture is a single strand of suture that is inserted through a hole formed in the distal end of the penile implant to provide two free ends of the single strand of suture, with each of the two free ends of the single strand of suture removable through the hole formed in the distal end of the penile implant. This configuration provides the suture with sufficient tensile strength to ensure that the suture accommodates the pulling force associated with placement of the implant in the penis.

The tow suture is a single strand of suture that is inserted through a hole formed in the distal end of the penile implant to provide two free ends of the single strand of suture, with the delivery cap coupled to the tow suture between the distal end of the penile implant and the two free ends of the single strand of suture. This configuration allows the delivery cap to be handled during an implantation procedure and manages the location of the ends of the suture.

An open slot is formed through an exterior surface of the needle, and the open slot is sized for engagement with the portion of the tow suture oriented in the aperture of the delivery cap. This configuration results in the tow suture automatically or effortlessly dropping into the slot formed in the needle, and also allows the tow suture to disengage from the needle after the tow suture is pushed through the glans penis.

A recess is formed in a proximal base of the delivery cap and a slotted opening is formed in a distal end of the delivery cap to custom fit the delivery cap to the tool and to ensure that the tow suture is engaged with the delivery cap during manufacture of the system.

A recess is formed in a longitudinal direction in a proximal base of the delivery cap, a slotted opening is formed in a lateral direction across a distal end portion of the delivery cap, and the aperture extends from the recess to the slotted opening. This configuration has the advantage of ensuring that unsuitable tools are not employed with the delivery cap; and also in ensuring that the needle will engage with the tow suture as the needle traverses the delivery cap.

The proximal end 102 of the delivery cap 25 is attachable to the distal tool end 28 of the insertion tool 20 and the slotted opening 112 is formed in the distal end 104 of the delivery cap. The aperture 110 is a located at a center of the delivery cap 25 and communicates from the proximal end 102 to the distal end 104 of the delivery cap. This configuration ensures that the tow suture will be engage by the needle as the needle passes through the delivery cap.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A system for implanting a penile prosthetic into a penis with an insertion tool having a needle, the system comprising:
    a penile implant having a proximal end insertable into a crus penis and a distal end insertable into a glans penis;
    a tow suture coupled to the distal end of the penile implant; and
    a delivery cap, a distal end portion of the delivery cap is curved, with the delivery cap having a length extending between a proximal end of the delivery cap that is attachable to the insertion tool and a distal end of the delivery cap;
    wherein the delivery cap has an aperture having an aperture diameter, with the aperture formed through the length of the delivery cap from the proximal end to the distal end of the delivery cap;
    wherein the tow suture is removably coupled to the delivery cap and disposed across the aperture diameter;
    wherein the needle of the insertion tool is configured to pass through the aperture and engage with the tow suture disposed across the aperture diameter.

2. The system of claim 1, wherein the delivery cap retains a portion of the tow suture within in the aperture for engagement of the needle of the insertion tool with the tow suture.

3. The system of claim 1, wherein a slotted opening is formed in the distal end portion of the delivery cap with the slotted opening coupled with the tow suture.

4. The system of claim 1, wherein a slotted opening is formed in a distal end portion of the delivery cap and the aperture communicates with the slotted opening.

5. The system of claim 1, wherein a slotted opening is formed in a distal end portion of the delivery cap with the slotted opening extending laterally across an entire diameter of the delivery cap.

6. The system of claim 1, wherein a slotted opening is formed in a distal end portion of the delivery cap with the slotted opening extending laterally across an entire outside diameter of the delivery cap, with a first gap formed in the slotted opening and measured where the slotted opening intersects with the aperture is smaller than a second gap formed in the slotted opening and measured where the slotted opening intersects with the outside diameter of the delivery cap.

7. The system of claim 1, wherein the proximal end of the delivery cap includes a proximal base having a recess that is sized to fit over an end of the insertion tool.

8. The system of claim 1, wherein the distal end portion of the delivery cap defines a hemispherical dome that is located opposite from a proximal base of the delivery cap, and the aperture extends longitudinally through the delivery cap between the proximal base and the hemispherical dome.

9. The system of claim 1, wherein the delivery cap has an outside diameter that is equal to an outside diameter of the insertion tool.

10. The system of claim 1, wherein the tow suture is inserted through a hole formed in the distal end of the penile implant.

11. The system of claim 1, wherein the needle includes an open slot formed through an exterior surface of the needle, with the open slot sized for engagement with the tow suture.

12. The system of claim 1, wherein a recess is formed in a proximal base of the delivery cap and a slotted opening is formed in the distal end portion of the delivery cap.

13. The system of claim 1, wherein the aperture is a located at a center of the delivery cap on a longitudinal axis of the delivery cap.

14. A system for implanting a penile prosthetic into a penis with an insertion tool having a needle, the system comprising:
    a penile implant having a proximal end insertable into a crus penis and a distal end insertable into a glans penis;
    a tow suture coupled to the penile implant; and
    a delivery cap provided separate from the penile implant and attachable to the insertion tool;
        wherein the delivery cap has an aperture that is formed longitudinally through the delivery cap, with the aperture sized to allow the needle of the insertion tool to pass through the aperture;
        wherein the delivery cap has an opening separate from the aperture, where the tow suture is insertable into the opening to removably couple the tow suture with the delivery cap.

15. The system of claim 14, wherein the tow suture is disposed across the aperture when inserted into the opening of the delivery cap.

* * * * *